United States Patent
Mimura et al.

(10) Patent No.: US 10,035,747 B2
(45) Date of Patent: Jul. 31, 2018

(54) METHOD FOR RECOVERING INERT MATERIAL AND METHOD FOR PRODUCING ACRYLIC ACID USING INERT MATERIAL RECOVERED BY SAID METHOD

(71) Applicant: NIPPON SHOKUBAI CO., LTD., Osaka (JP)

(72) Inventors: Yasuhiro Mimura, Hyogo (JP); Fumio Munechika, Hyogo (JP); Hisao Kakuta, Hyogo (JP); Motoki Hisanaga, Hyogo (JP); Seiichi Hara, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/500,238

(22) PCT Filed: Jul. 30, 2015

(86) PCT No.: PCT/JP2015/071577
§ 371 (c)(1),
(2) Date: Jan. 30, 2017

(87) PCT Pub. No.: WO2016/017722
PCT Pub. Date: Feb. 4, 2016

(65) Prior Publication Data
US 2017/0260118 A1    Sep. 14, 2017

(30) Foreign Application Priority Data
Aug. 1, 2014 (JP) .................... 2014-158208

(51) Int. Cl.
*C07C 51/235* (2006.01)
*B08B 3/08* (2006.01)
*B08B 3/10* (2006.01)

(52) U.S. Cl.
CPC .............. *C07C 51/235* (2013.01); *B08B 3/08* (2013.01); *B08B 3/106* (2013.01)

(58) Field of Classification Search
None
See application file for complete search history.

(56) References Cited

U.S. PATENT DOCUMENTS

| 4,873,368 A | 10/1989 | Kadowaki et al. |
| 6,069,271 A | 5/2000 | Tanimoto et al. |

(Continued)

FOREIGN PATENT DOCUMENTS

| CN | 101822959 | 9/2010 |
| JP | 5673041 | 6/1987 |

(Continued)

OTHER PUBLICATIONS

International Search Report dated Oct. 13, 2015 in International (PCT) Application No. PCT/JP2015/071577.

(Continued)

*Primary Examiner* — Clinton A Brooks
(74) *Attorney, Agent, or Firm* — Wenderoth, Lind & Ponack, L.L.P.

(57) ABSTRACT

The present invention provides a method for allowing a used inert material that has been subjected to a reaction once, which is disposed of in the background art, to be used again as well as a brand-new one. A method of recovering an inert material of the present invention is characterized by in the fixed-bed reactor, the inert material is loaded in an inert material layer provided between a first-stage catalyst layer and a second-stage catalyst layer, the first-stage catalyst layer is loaded with a first-stage catalyst for producing acrolein from propylene, and the second-stage catalyst layer is loaded with a second-stage catalyst for producing acrylic acid from acrolein, the method comprising the steps of:

(Continued)

extracting the inert material from the fixed-bed reactor; washing the extracted inert material; and screening the washed inert material.

5 Claims, 1 Drawing Sheet

(56) References Cited

U.S. PATENT DOCUMENTS

| | | |
|---|---|---|
| 6,994,833 B1 | 2/2006 | Nishimura et al. |
| 2006/0135346 A1 | 6/2006 | Nakamura et al. |
| 2008/0021240 A1 | 1/2008 | Tanimoto et al. |
| 2008/0021242 A1 | 1/2008 | Tanimoto et al. |
| 2009/0000992 A1 | 1/2009 | Dufresne et al. |
| 2009/0088316 A1 | 4/2009 | Nakamura et al. |
| 2009/0112367 A1 | 4/2009 | DeCourcy et al. |
| 2011/0178334 A1* | 7/2011 | Tanimoto ............. C07C 45/35 562/598 |

FOREIGN PATENT DOCUMENTS

| | | |
|---|---|---|
| JP | 11-130722 | 5/1999 |
| JP | 2005-95874 | 4/2005 |
| JP | 3646027 | 5/2005 |
| JP | 2007-289810 | 11/2007 |
| JP | 2008-24644 | 2/2008 |
| JP | 2008-43937 | 2/2008 |
| JP | 2011-504795 | 2/2011 |
| JP | 5559692 | 7/2014 |
| WO | 2010/032665 | 3/2010 |

OTHER PUBLICATIONS

English translation of Japanese Office Action dated Oct. 17, 2017 in corresponding Japanese Application No. 2016-538413.
Office Action dated Jan. 17, 2017 in corresponding Taiwanese Application No. 104124861, with English translation.
Extended European Search Report dated Feb. 20, 2018 in European Application No. 15828031.3.

* cited by examiner

U S 10,035,747 B2

METHOD FOR RECOVERING INERT MATERIAL AND METHOD FOR PRODUCING ACRYLIC ACID USING INERT MATERIAL RECOVERED BY SAID METHOD

TECHNICAL FIELD

The present invention relates to a method for recovering an inert material which is used in production of acrylic acid by subjecting propylene to two-stage catalytic gas phase oxidation, and a method for producing acrylic acid using the inert material recovered by said method.

BACKGROUND ART

Among methods of producing acrylic acid, two-stage catalytic gas phase oxidation of propylene is most commonly and widely used in industry. This method includes a first-stage reaction for catalytic gas phase oxidation of propylene to acrolein, and a second-stage reaction for catalytic gas phase oxidation of acrolein to acrylic acid. Methods for performing these reactions which are conventionally proposed are roughly divided into the following two methods: a method of using a single reactor equipped with a plurality of reaction tubes each having a first-stage catalyst layer loaded with a catalyst suitable for the first-stage reaction (hereinafter referred to as a "first-stage catalyst") and a second-stage catalyst layer loaded with a catalyst suitable for the second-stage reaction (hereinafter referred to as a "second-stage catalyst"); and a method of using two reactors, i.e., a first-stage reactor equipped with a plurality of reaction tubes loaded with a first-stage catalyst and a second-stage reactor equipped with a plurality of reaction tubes loaded with a second-stage catalyst.

In the former method, an inert material is additionally loaded between the first-stage catalyst and the second-stage catalyst. In general, the reaction temperature of the first-stage catalyst layer is higher than the reaction temperature of the second-stage catalyst layer. Therefore, by providing the inert material layer, acrolein-containing reaction gas can be rapidly cooled so that the temperature of the gas is reduced to a temperature range suitable for the oxidation reaction in the second-stage catalyst layer (Patent Literature 1). However, when the production of acrylic acid is performed for a long period of time, impurities (e.g., high-boiling materials, carbides, and the like which are by-products of the first-stage reaction) or the like will stick to the surface of the inert material, which leads to a problem that the reaction tube loaded with the catalysts and the inert material is blocked. If the reaction is continued with the blocked reaction tube, a pressure loss will increase, which may lead to a runaway reaction. Therefore, it is necessary to regularly extract the inert material from the fixed-bed reactor, and clean the reaction tubes when necessary. In addition, in order to extract the inert material from the reaction tubes, it is necessary to push out the inert material to which impurities or the like are firmly sticking using a rod or the like, or suck out the inert material using a suction tube or the like, and these operations disadvantageously distort and deform the inert material.

Also, typically, the inert material extracted from the reactor is mixed with the catalyst. There are known methods of separating a catalyst from an auxiliary filler (inert material) having a shape similar to the catalyst, particularly a method of separating a catalyst from an auxiliary filler made of a magnetic metal by collecting the magnetic metal auxiliary filler using a magnet (Patent Literature 2).

CITATION LIST

Patent Literature

Patent Literature 1: JP H11-130722 A
Patent Literature 2: JP 2007-289810 A
Patent Literature 3: JP 5559692 B
Patent Literature 4: JP 2008-043937 A
Patent Literature 5: JP 3646027 B

SUMMARY OF INVENTION

Technical Problem

In the background art, in addition to the problem that the inert material is distorted and deformed when the inert material is extracted from the reactor, impurities such as high-boiling materials, carbides, and the like which occur during the reaction, or metal components such as molybdenum and the like which sublime from the catalyst, firmly stick to the inner surface as well as the outer surface of the inert material. If the extracted inert material is mixed with a distorted and deformed inert material, then when the inert material is directly reused, a bridge or the like will occur during loading of the inert material into a reactor, which may lead to a runaway reaction. Alternatively, even when the outer shape is intact, high-boiling materials, impurities, and the like which stick to the surface of the inert material may lead to an increase in pressure loss or a blockage in the reactor.

These problems are indicated also by literature. For example, Patent Literature 3 discloses an inert material having a characteristic shape, and includes the explanation "As the inert material, a recycled material may be used" (paragraph [0039]). However, Patent Literature 3 does not describe actual reuse of a recovered inert material. Patent Literature 4 indicates that if retention of gas occurs somewhere in a reactor, the operation is hindered (paragraph [0009], [0021], [0040], and [0049]). Furthermore, Patent Literature 5 includes the explanation " . . . action or function of the inert refractory material layer (i.e., a layer made of an inert material) is to prevent a pressure loss due to impurities . . . and the like contained in the reaction gas when the reaction gas is passed from the upstream reaction layer." Patent Literature 5 also illustrates a molybdenum component subliming from an upstream catalyst, a high-boiling material such as terephthalic acid or the like as a by-product, and the like as the impurities in a case where acrylic acid is produced (paragraph [0034]). In other words, according to Patent Literature 5, it is known that the reaction tube is likely to be blocked by impurities generated during production of acrylic acid, and it can be understood that, in the background art, this problem is addressed by capturing the impurities using, for example, an inert refractory material layer having a voidage of 40 to 99.5% (paragraphs [0034] and [0035]). In view of the above common technical knowledge, it is understood that the reuse of the inert material is not common in the background art, and particularly, it is difficult to reuse the deformed inert material which is likely to lead to retention of gas in the reactor, and the inert material to which impurities stick. Even when the deformed inert material is reused, the operation may be hindered by retention of gas, resulting in a decrease in operation time. Also, the inert material to which impurities stick may lead to an increase in pressure loss. Therefore, in the background art, it is common for the inert material that has been subjected to a reaction once to be disposed of and replaced with a brand-new inert material, which is considerably uneconomical.

Under these circumstances, it is an object of the present invention to provide a method for allowing a used inert material which is disposed of in the background art and that has been subjected to a reaction once to be used again as well as a brand-new one.

Solution to the Problems

The present inventors have extensively studied and attempted to achieve the above object. As a result, the present inventors have found that the used inert material, which is disposed of in the background art, is washed and then screened, whereby the inert material can be recovered in approximately mint condition, and the recovered inert material can be reused to produce acrylic acid from propylene in the same way as when a brand-new one is used, and have made the present invention.

That is, a method of recovering an inert material of the present invention is characterized by in the fixed-bed reactor, the inert material is loaded in an inert material layer provided between a first-stage catalyst layer and a second-stage catalyst layer, the first-stage catalyst layer is loaded with a first-stage catalyst for producing acrolein from propylene, and the second-stage catalyst layer is loaded with a second-stage catalyst for producing acrylic acid from acrolein, the method comprising the steps of; extracting the inert material from the fixed-bed reactor; washing the extracted inert material; and screening the washed inert material. Additionally, it is preferable that the screening step comprises the steps of; determining quality for screening the inert material, and then separating the inert material. Further, it is preferable that a determination means is used in the determination step, and an image processing device is used as the determination means.

Additionally, the present invention involves a method of producing acrylic acid, comprising the steps of; recovering the inert material by the above method; and subjecting propylene to catalytic gas phase oxidation by introducing the propylene into a fixed-bed reactor having a first-stage catalyst layer loaded with a first-stage catalyst for producing acrolein from propylene, a second-stage catalyst layer loaded with a second-stage catalyst for producing acrylic acid from acrolein, and an inert material layer provided between the first-stage catalyst layer and the second-stage catalyst layer and loaded with at least a portion of the recovered inert material.

Advantageous Effects of the Invention

According to the present invention, an inert material that has been subjected to a reaction once, i.e., has been used once, can be recovered in approximately mint condition, and can be used again in production of acrylic acid.

DESCRIPTION OF EMBODIMENTS

As used herein, the term "brand-new inert material" (may also be simply referred to as a "brand-new material") refers to an inert material that has not once been loaded into a reactor or subjected to a reaction, i.e., has not once been used. As used herein, the term "recycled inert material" (may also be simply referred to as a "recycled material") refers to an inert material that has been loaded into a reactor or subjected to a reaction at least once, i.e., has been used at least once, and has been extracted and washed using a method described herein (followed by drying as necessary), and screened using a method according to the present invention. Here, to screen means an action of screening using predetermined criteria. Also, the term "extracted inert material" (may also be simply referred to as a "extracted material") refers to an inert material that has been loaded into a reactor or subjected to a reaction at least once, i.e., has been used at least once, and has been extracted and washed using a method described herein, and then dried as necessary.

<Production of Acrylic Acid>

In production of acrylic acid according to the present invention, used is a fixed-bed reactor having a first-stage catalyst layer loaded with a first-stage catalyst for producing acrolein from propylene, a second-stage catalyst layer loaded with a second-stage catalyst for producing acrylic acid from acrolein, and an inert material layer loaded with an inert material between the first-stage catalyst layer and the second-stage catalyst layer.

Examples of such a fixed-bed reactor are illustrated. As a first embodiment, an example of the fixed-bed reactor includes a single reactor equipped with a plurality of reaction tubes each having a first-stage catalyst layer loaded with a first-stage catalyst and a second-stage catalyst layer loaded with a second-stage catalyst. In this case, an inert material layer is provided between the first-stage catalyst layer and the second-stage catalyst layer. In other words, at least three layers, i.e., the first-stage catalyst layer, the inert material layer, and the second-stage catalyst layer, are provided in each reaction tube. As a second embodiment, an example of the fixed-bed reactor includes two reactors, i.e., a first-stage reactor equipped with a plurality of reaction tubes loaded with a first-stage catalyst, and a second-stage reactor equipped with a plurality of reaction tubes loaded with a second-stage catalyst. In this case, a portion of the reaction tube of the first-stage reactor which is loaded with the first-stage catalyst corresponds to a first-stage catalyst layer, and a portion of the reaction tube of the second-stage reactor which is loaded with the second-stage catalyst corresponds to a second-stage catalyst layer. In this case, an inert material layer may be provided in the first-stage reactor closer to the outlet thereof than is the first-stage catalyst layer, or may be provided in the second-stage reactor closer to the inlet thereof than is the second-stage catalyst layer, or may be provided in a tube which connects the first-stage reactor and the second-stage reactor. Note that the "inlet" and "outlet" mean a portion of the reactor through which gas is introduced and a portion of the reactor through which gas is discharged, respectively.

The first-stage catalyst is not particularly limited if it can convert propylene into acrolein by catalytic gas phase oxidation, and may be a known and commonly used oxide catalyst. Specifically, as the first-stage catalyst, an oxide catalyst represented by the following general formula (I) can be preferably used.

(I)

$$Mo_aBi_bFe_cX1_dX2_eX3_fX4_gO_x \quad (I)$$

(where Mo represents molybdenum, Bi represents bismuth, Fe represents iron, X1 represents at least one element selected from the group consisting of cobalt and nickel, X2 represents at least one element selected from the group consisting of alkali metals, alkaline-earth metals, boron, and thallium, X3 represents at least one element selected from the group consisting of tungsten, silicon, aluminum, zirconium, and titanium, X4 represents at least one element selected from the group consisting of phosphorus, tellurium, antimony, tin, cerium, lead, niobium, manganese, arsenic, and zinc, O represents oxygen, and a, b, c, d, e, f, g, and x represent the atomic ratios of Mo, Bi, Fe, X1, X2, X3, X4, and O, respectively, and when a=12, then b=0.1 to 10, c=0.1 to 20, d=2 to 20, e=0.001 to 10, f=0 to 30, and g=0 to 4, and x is a numerical value that is determined by the oxidation state of each element.)

The second-stage catalyst is not particularly limited if it can convert acrolein into acrylic acid by catalytic gas phase oxidation, and may be a known and commonly used oxide catalyst. Specifically, as the second-stage catalyst, an oxide catalyst represented by the following general formula (II) can be preferably used.

$$Mo_h V_i W_j Y1_k Y2_l Y3_m Y4_n O_y \quad (II)$$

(where Mo represents molybdenum, V represents vanadium, W represents tungsten, Y1 represents at least one element selected from the group consisting of antimony, bismuth, chromium, niobium, phosphorus, lead, zinc, cobalt, nickel, and tin, Y2 represents at least one element selected from the group consisting of copper and iron, Y3 represents at least one element selected from the group consisting of alkali metals, alkaline-earth metals, and thallium, Y4 represents at least one element selected from the group consisting of silicon, aluminum, titanium, zirconium, yttrium, rhodium, and cerium, O represents oxygen, and h, i, j, k, l, m, n, and y represent the atomic ratios of Mo, V, W, Y1, Y2, Y3, Y4, and O, respectively, and when h=12, then i=2 to 14, j=0 to 12, k=0 to 5, l=0.01 to 6, m=0 to 5, and n=0 to 10, and y is a numerical value that is determined by the oxidation state of each element.)

As a method of molding these catalysts, a conventional and widely known method may be employed. For example, extrusion molding, tableting molding, or the like in which an active component is molded into a predetermined shape, can be employed. Alternatively, the catalysts can be produced by a method of supporting an active component on any inert carrier having a predetermined shape (e.g., alumina, silica, silica-alumina, titania, magnesia, steatite, silica-magnesia, silicon carbide, silicon nitride, zeolite, etc.).

The shape of each catalyst or the inert carrier is not particularly limited, and may be any shape, such as spherical, cylindrical, annular, indefinite, or the like. Needless to say, when the shape is spherical, the shape does not need to be perfectly spherical, and may be substantially spherical. The same applies to cylindrical and annular shapes.

The first-stage catalyst is loaded into the first-stage catalyst layer, and the second-stage catalyst is loaded into the second-stage catalyst layer. The first-stage catalyst and the second-stage catalyst may be of the same type or of different types having different activities or shapes. For example, the first-stage catalyst layer and the second-stage catalyst layer may each include multiple layers loaded with different catalysts, or a single layer containing a mixture of two or more catalysts. Also, a portion of the catalysts may be diluted with an inert carrier or the like.

The loading specifications and reaction conditions of the catalysts and the inert material can be the same as those for known methods, such as those described in JP S54-21966 A, JP H01-165543 A, and Patent Literature 1, except for the use of the above inert material.

The fixed-bed reactor may be a fixed bed-type shell-and-tube heat exchanging reactor, and each reaction tube provided in the fixed-bed reactor may be a typical one having a circular cross section. The inner diameter of each reaction tube is preferably 15 mm or more, more preferably 20 mm or more, and even more preferably 22 mm or more, although it is not particularly limited if each reaction tube can be loaded with a catalyst and an inert material. The upper limit of the inner diameter of each reaction tube is preferably 50 mm or less, more preferably 40 mm or less, and even more preferably 38 mm or less. The length of each reaction tube is, for example, preferably within the range of 1 m to 10 m, although it is determined, depending on the capabilities of related apparatuses, and the like.

The inert material is not particularly limited if it is substantially inactive against acrolein-containing reaction gas (note that the acrolein-containing reaction gas contains, in addition to acrolein, propylene as a starting material, acrylic acid as an target product, by-products such as terephthalic acid and the like, and impurities). Examples of the inert material include metals, carbon, and plastics. More preferable examples of the inert material include a-alumina, alundum, mullite, carborundum, silicon carbide, steatite, earthenware, porcelain, stainless steel (SUS), iron, various ceramics, and the like. Among them, stainless steel is particularly preferable in terms of heat conductivity and corrosion resistance. The type of stainless steel is not particularly limited. For example, a SUS400-series stainless steel having magnetism is preferable, since, if the inert material is made of the SUS400-series stainless steel, the inert material can be easily separated from the catalyst and recovered using a magnet after the inert material has been used. Examples of the SUS400-series stainless steel include SUS403, SUS405, SUS410, SUS430, SUS434, and the like.

Although the shape of the inert material is not particularly limited, but it is preferably hollow cylindrical. Here, the term "hollow cylindrical" refers to a hollow circular column shape which has a generally circular cross section. Examples of the hollow cylindrical shape include Raschig rings, Pall rings, cross rings, cascade mini-rings, and the like. Alternatively, the inert material may have the shape of a tube having a side surface comprising an opening, as disclosed in Patent Literature 3 or the like.

The hollow cylindrical inert material has an outer diameter of preferably 3 to 30 mm and more preferably 6 to 15 mm, and has a thickness of preferably 0.1 to 3 mm and more preferably 0.3 to 1 mm (note that the outer diameter is more than two times as great as the thickness). The inert material also has an axial length (height) of preferably 3 to 30 mm and more preferably 6 to 15 mm.

The inert material is loaded into the inert material layer. Therefore, the inert material layer needs to have a sufficient length to rapidly cool the acrolein-containing reaction gas. The length of the inert material layer needs to be selected as appropriate depending on reaction conditions such as the composition and concentration of raw material gas, reaction temperature, and the like. The length of the inert material layer is, for example, preferably 100 mm or more and 1,000 mm or less, and more preferably 200 mm or more and 800 mm or less.

At the beginning of operation of the fixed-bed reactor, the inert material loaded in the inert material layer may be all recycled inert materials, a mixture of a brand-new material and a recycled material, or all brand-new materials, more preferably may be a mixture of a brand-new material and a recycled material, or all recycled materials. The inert material does not necessarily need to be uniformly loaded throughout the inert material layer. However, it is preferable to load the inert material substantially uniformly throughout the inert material layer so that autoxidation of the acrolein-containing reaction gas can be inhibited or the acrolein-containing reaction gas can be efficiently cooled.

Next, a method for producing acrylic acid will be described. In the method for producing acrylic acid, the above fixed-bed reactor is used to produce acrylic acid from propylene. Specifically, a method for producing acrylic acid according to the present invention includes a step of introducing propylene and subjecting the propylene to catalytic gas phase oxidation using a fixed-bed reactor according to the present invention. Particularly, the method includes a first-stage reaction step of introducing propylene into the first-stage catalyst layer and subjecting the propylene to catalytic gas phase oxidation to produce acrolein, a step of introducing a reaction gas discharged from the first-stage catalyst layer into the second-stage catalyst layer through the inert material layer, and a second-stage reaction step of subjecting the acrolein to catalytic gas phase oxidation in the second-stage catalyst layer to produce acrylic acid.

A preferable reaction temperature of the first-stage reaction or the second-stage reaction is selected as appropriate depending on reaction conditions such as the composition of raw material gas and space velocity, or the like. In the first-stage reaction, the reaction temperature is typically within the range of 300° C. to 380° C. In the second-stage reaction, the reaction temperature is typically within the range of 250° C. to 350° C. Generally, the temperature of the first-stage reaction is set to be higher than the temperature of the second-stage reaction. Specifically, the difference in reaction temperature between the first-stage reaction and the second-stage reaction is 10° C. to 110° C. and preferably 30° C. to 80° C. Note that the reaction temperature of the first-stage reaction and the reaction temperature of the second-stage reaction each substantially correspond to the temperature at the heating medium inlet of the respective reactor or catalyst layer.

<Method for Recovering Inert Material>

When the production of acrylic acid is performed for a certain period of time, impurities such as high-boiling materials, carbides, and the like, or metal components such as molybdenum and the like which sublime from the catalyst, will stick to the outer surface and/or inner surface of the inert material. When the amount of such sticking materials increases, the reaction tube becomes blocked and thus the reaction efficiency may decrease. With this in mind, in the present invention, the inert material that has been subjected to a reaction once, i.e., has been used once, is recovered by extracting the inert material from the fixed-bed reactor, washing the extracted inert material, and screening the washed inert material.

<Extraction Step>

The method of extracting the inert material loaded in the reactor is not particularly limited. The inert material loaded in the reactor may be extracted by striking it with a piano wire, pushing it out using a rod, or the like. Alternatively, the inert material may be extracted by suction using a suction tube, as disclosed in JP 2002-301355 A.

In this case, the extracted inert material is mixed with the catalyst. Therefore, it is desirable to separate the inert material from the catalyst. The method of separating the inert material from the catalyst is not particularly limited. The separation method may be selected as appropriate from screening depending on the difference in specific gravity, sieving as disclosed in JP 2005-95874 A, shape separation, fragmentation and classification, separation using a magnet as disclosed in Patent Literature 2, and the like, depending on conditions.

<Washing Step>

The inert material can, for example, be washed by water washing with water, alkali washing with an alkaline solution, acid washing with an acidic solution, ultrasonic washing with ultrasonic waves, or the like. In particular, alkali washing is preferable. Conditions for washing may be set as appropriate. For example, in the case of water washing, the used inert material may be mixed with water, and washing may be performed at 15 to 100° C. (boiled state) for about 1 to 10 hr. In the case of alkali washing, the used inert material may be mixed with an alkaline solution, and washing may be performed at 15 to 100° C. (boiled state) for about 1 to 10 hr. Examples of an alkaline material which can be used include sodium hydroxide, potassium hydroxide, calcium hydroxide, ammonia, and the like. The concentration of the alkaline material may be within the range of 1 to 10 mass % and preferably 2 to 8 mass %. After alkali washing or acid washing, alkali or acid remains sticking to the surface or the like of the inert material, and therefore, it is preferable to perform water washing after alkali washing or acid washing. In the washing step, it is not always necessary to perfectly wash off the sticking high-boiling materials, impurities, or the like. The washing is sufficient if the resulting inert material can be reused, particularly, about 70% of the used inert material can be recovered by the screening step described below.

The washed inert material may also be dried. The drying method is not particularly limited if it can dry the inert material. Examples of the drying method include drying by heating in the presence of air or inert gas atmosphere using a box dryer, tunnel dryer, or the like, drying using a vacuum dryer, and the like.

<Screening Step>

Next, the screening step of screening the inert material washed in the above washing step, i.e., the extracted inert material, is performed. In the recovery method of the present invention, it is important to perform the screening step. The extracted inert material contains an inert material that has been distorted and deformed in the extraction step. The study by the present inventors has demonstrated that (i) the deformed inert material has an irregular shape, and (ii) a very small amount of carbides, a molybdenum component subliming from the catalyst, high-boiling-point impurities such as terephthalic acid and the like are likely to remain sticking to the inert material even after the washing step, which cause a problem. Examples of the problem caused by (i) include a problem that acrolein is likely to undergo autoxidation, since the gas is retained at a "deformed portion (i.e., a portion having an irregular shape)." Particularly, precipitation of high-boiling-point impurities is most likely to occur in the inert material layer as a cooling portion, and therefore, accumulation of carbides is accelerated at that portion, leading to a blockage in the reactor or an increase in pressure loss, and thereby it is also illustrated resulting in shut-down of the operation in a shorter time. Examples of the problem caused by (i) also include: a problem that the height of the layer is uneven in each reaction tube, which causes different pressure losses, so that the operation becomes unstable; a problem that a bridge or the like occurs during loading of the reactor, which may lead to a runaway reaction; and the like. Examples of the problem caused by (ii) include a problem that if the inert material to which carbides or high-boiling-point impurities remain sticking is loaded into the reaction tube again and the operation is performed, the carbides or high-boiling-point impurities cause acceleration of additional sticking of carbides, resulting in shut-down of the operation in a short time; and the like. However, the deformed inert material can be removed by performing the screening step, whereby the above troubles can be improved.

Note that, as to an influence of the pressure loss on the reaction for producing acrylic acid, for example, results of experiment examples of Patent Literature 3 show that when the pressure loss per unit layer length (1 m) increases by about 0.1 kPa, the propylene conversion rate and the acrylic acid yield decrease by about 0.1 mol %. At present, the annual global production of acrylic acid is about several millions of tons. In view of this fact, it is needless to say that a yield difference of about 0.1 mol % is huge.

In the screening step, screening can be performed using a sieve or the like. However, the screening step preferably includes the steps of determining quality for screening the inert material, and separating the inert material. Criteria for determining the quality in the determination step (may also be simply referred to as the "criteria") may be determined as appropriate depending on the shape, size, or the like of the inert material to be recovered.

As a determination means in the determination step, visual determination may be employed. Alternatively, a machine is preferably used because of higher efficiency and higher determination accuracy, and in addition, a reduction in cost of the determination work. Among other things, an image processing device is preferably used. The image processing device refers to a device that captures an image of an object using an image capture unit, such as a CCD camera or the like, then converts the captured image into binary data using an image processing unit, subjects the binary data to a pre-process such as illumination correction or the like, and thereafter determines the shape of the object by performing a measuring process such as pattern matching or the like to determine whether or not certain criteria (e.g., criteria below) are satisfied, using a checking unit.

Examples of the criteria include whether or not a cross-sectional shape of the inert material is deformed to exceed a range set by a specific value, whether or not sticking impurities have a predetermined thickness or more, whether or not a clearance at a seam in the inert material, if any, is excessively large, and the like. Specifically, when the shape of the inert material is hollow cylindrical, it may be determined whether or not the cross-sectional shape (circular shape) thereof satisfies the following criteria:

(1) the diameter (outer diameter) is within ±20% of a reference value before use, preferably within ±15% thereof, and more preferably within ±10% thereof;

(2) the matter sticking to the surface and inside of the material, whose thickness is 1.0 mm or more, preferably 0.8 mm or more, and more preferably 0.5 mm or more, is not contained; and (3) a clearance at a seam is 4 mm or less, preferably 2 mm or less, and more preferably 1 mm or less (if the inert material has a seam). Here, it is preferable to use the image processing device because it can be instantaneously determined whether or not the above criteria are satisfied.

As a separation means in the separation step, the separation may be performed manually by a human. Alternatively, the separation is preferably performed using a machine because of higher efficiency and a reduction in cost of the separation work. Examples of the separation means include a means for instantaneously blowing off either a material that has been determined as good or a material that has been determined as defective (i.e., a preset one of a good material and a defective material) using compressed gas, such as air or the like, for separation, a method of physically rejecting a preset one of a good material and a defective material on a separation line, or switching lines instantaneously, for separation, and the like.

<Loading of Recycled Material>

Thereafter, the inert material recovered through the screening step can also be loaded into a fixed-bed reactor to produce acrylic acid. The fixed-bed reactor has a first-stage catalyst layer loaded with a first-stage catalyst for producing acrolein from propylene, a second-stage catalyst layer loaded with a second-stage catalyst for producing acrylic acid from acrolein, and an inert material layer between the first-stage catalyst layer and the second-stage catalyst layer. At least a portion of the recovered inert material may be loaded into the inert material layer. Each of the fixed-bed reactor, the first-stage catalyst, the first-stage catalyst layer, the inert material layer, the second-stage catalyst, and the second-stage catalyst layer may be the same as or different from that described above.

In the production of acrylic acid, the above conditions may be used as appropriate. Specifically, acrylic acid is produced from propylene in the fixed-bed reactor. More particularly, the method for producing acrylic acid includes a step of introducing and subjecting propylene to catalytic gas phase oxidation in the fixed-bed reactor. Specifically, the method for producing acrylic acid includes a first-stage reaction step of introducing propylene into the first-stage catalyst layer and subjecting the propylene to catalytic gas phase oxidation to produce acrolein, a step of introducing a reaction gas discharged from the first-stage catalyst layer into the second-stage catalyst layer through the inert material layer, and a second-stage reaction step of subjecting the acrolein to catalytic gas phase oxidation in the second-stage catalyst layer to produce acrylic acid.

The inert material recovered after the screening step is loaded into the inert material layer (of the reaction tube) again. In this case, the inert material loaded in the inert material layer may be all recycled inert materials or a mixture of a brand-new material and a recycled material. Examples of a method of loading a mixture of a brand-new material and a recycled material include: a method of loading a uniform mixture of a brand-new material and a recycled material; a method of loading a recycled material before loading a brand-new material; a method of loading a brand-new material before loading a recycled material; a method of loading a brand-new material and a recycled material so that a layer of the brand-new material and a layer of the recycled material are alternately formed; and the like.

The timing at which the inert material is recovered and reused are not particularly limited. Both the recovery and the reuse may be performed during shut-down of the operation of the reactor for replacement of the catalysts of the first-stage catalyst layer and/or the second-stage catalyst layer.

This application claims priority to Japanese Patent Application No. 2014-158208 filed on Aug. 1, 2014, the entire disclosure of which is incorporated by reference herein.

Examples

The present invention will now be specifically described by way of examples. The present invention is not intended to be limited to examples described below, and can also be carried out with appropriate modifications within the range adaptable to the present invention, and such modifications are included in the technical scope of the present invention.

Note that the propylene conversion rate and the acrylic acid yield are calculated using the following equations:

Propylene conversion rate [mol %]=(the amount of reacted propylene in moles)/(the amount of supplied propylene in moles)×100

Acrylic acid yield [mol %]=(the amount of produced acrylic acid in moles)/(the amount of supplied propylene in moles)×100

<First-Stage Catalyst>

As the first-stage catalyst, a catalyst was prepared by extrusion molding of a catalyst component. The catalyst component had the following metal composition excluding oxygen and shape (average).

$Mo_{12}Bi_{1.1}Fe_{0.9}Co_{5.8}Ni_{1.1}W_{0.6}Si_{2.0}K_{0.06}$

First-stage catalyst 1: hollow cylindrical shape of 6 mm (outer diameter)×3 mm (inner diameter)×7 mm (height)

First-stage catalyst 2: hollow cylindrical shape of 8 mm (outer diameter)×4 mm (inner diameter)×8.5 mm (height)

<Second-Stage Catalyst>

As the second-stage catalyst, a catalyst supporting a catalyst component on a silica-alumina spherical carrier was prepared. The catalyst component had the following metal composition excluding oxygen and shape (average).

$Mo_{12}V_{5.0}W_{1.3}Cu_{1.7}Co_{0.8}Sb_{0.5}$

Second-stage catalyst 1: spherical shape of 6.5 mm (outer diameter)

Second-stage catalyst 2: spherical shape of 8 mm (outer diameter)

<Inert Material>

As the inert material, an inert material made of SUS410 and having an annular shape (hollow cylindrical shape) of 7.5 mm (outer diameter)×7.5 mm (height) and 0.7 mm (thickness) was prepared.

<Reactor>

In a fixed-bed shell-and-tube reactor including about 9,500 reaction tubes (each reaction tube has an inner diameter of 25 mm and a length of 6,000 mm) and a shell which covers the tubes and through which a heating medium is passed, the first-stage catalyst 2, the first-stage catalyst 1, the inert material made of SUS410, the second-stage catalyst 2, and the second-stage catalyst 1 were dropped and loaded from a top portion of each reaction tube in that order so that they have the following respective lengths: 900 mm (first-stage catalyst 2); 1,900 mm (first-stage catalyst 1); 500 mm (inert material); 800 mm (second-stage catalyst 2); and 1,900 mm (second-stage catalyst 1). Note that a partition plate having a thickness of 50 mm which divides the shell into an upper shell space portion and a lower shell space portion was provided at a height of 3,000 mm from the bottom of the shell, and the heating medium was circulated from bottom to top in each of the upper and lower shell space portions.

<Oxidation Reaction>

A gas mixture of 8.0 volume % of propylene, 15 volume % of oxygen, 7.5 volume % of water vapor, and the balance consisting of nitrogen was introduced as raw material gas from a bottom portion of the reactor set to a reaction temperature described below, at a space velocity of 1,700 $h^{-1}$ (STP) with respect to the first-stage catalyst, to undergo catalytic gas phase oxidation. The results are shown in Table 1.

[Initial Reaction Temperature]

The temperature of the first-stage catalyst layer (the temperature at the heating medium inlet of the lower shell space portion): 320° C.

The temperature of the second-stage catalyst layer (the temperature at the heating medium inlet of the upper shell space portion): 265° C.

TABLE 1

| Elapsed time (hr) | Propylene conversion rate (mol %) | Acrylic acid yield (mol %) | Temperature of second-stage catalyst layer (° C.) |
|---|---|---|---|
| 48 hr after start of reaction | 97.8 | 89.6 | 265 |
| 12,000 hr | 97.2 | 88.4 | 276 |

After 12,000 hr had elapsed, an increase in the heating medium temperature in the second-stage catalyst layer and a decrease in the yield of acrylic acid were observed.

<Extraction of Catalyst and Inert Material, Separation, Washing, and Drying>

After 12,000 hr had elapsed since the start of the reaction, the reaction was stopped. The second-stage catalyst 1, the second-stage catalyst 2, and the inert material were extracted from a top portion of the reactor by suction using a suction tube.

The extracted catalyst and inert material were separated from each other using an electromagnet. The inert material obtained by the separation was immersed in a 4-mass % NaOH aqueous solution, and the temperature thereof was increased by vapor using a fin tube heat exchanger, to perform washing by boiling for 1.5 hr (alkali washing). After the alkali washing, the inert material was further washed with water.

After the washing with water, the inert material was spread on a metal mesh vat, which was then placed into a box dryer at 60° C. and dried for 3.5 hr.

<Screening of Inert Material>

The quality of the dried inert material was determined using an image processing device. A defective material which does not satisfy criteria described below was instantaneously blown off and removed by compressed air. When the cross-sectional shape (circular shape) of the inert material satisfied the following criteria, it was determined that the inert material is good, and the inert material was recovered as a recycled material:

(1) the diameter (outer diameter) is within ±10% of a reference value before use;

(2) the matter sticking to the surface and inside of the material, whose thickness is 0.5 mm or more, is not contained; and (3) a clearance at a seam is 2 mm or less. Otherwise, it was determined that the inert material is defective. As a result, the recovery rate of the good inert material was about 95%.

Here, the recovery rate was calculated by the following equation.

Recovery rate(%)=(the weight of the good inert material used in the screening step which satisfies the criteria)/(the total weight of the washed inert material used in the screening step)×100

<Loading of Recycled Material and Reaction>

The first-stage catalysts were not replaced. The second-stage catalyst 1 and the second-stage catalyst 2 that had not been used, and the recycled inert material obtained in the screening step were loaded under the same loading conditions. The reaction was started under the same conditions. Note that the recovery rate of the inert material in the screening step was 95%, and therefore, when the inert material was loaded, the recycled material was loaded, and thereafter, a brand-new inert material was added to cover a shortfall to form an inert material layer. The results after the start of the reaction are shown in Table 2.

TABLE 2

| Elapsed time (hr) | Propylene conversion rate (mol %) | Acrylic acid yield (mol %) | Temperature of second-stage catalyst layer (° C.) |
|---|---|---|---|
| 48 hr after start of reaction | 97.8 | 89.5 | 265 |
| 12,000 hr | 97.2 | 88.3 | 277 |

Even when the recycled material was used as the inert material, the results after 12,000 hr had elapsed were similar to those when a brand-new inert material was used. It can be understood that the reaction can be continued without a problem even when the recycled material is used.

<Pressure Loss>

A pressure loss in the inert material layer of the reactor was measured by using 200 g of the inert material (recycled material; Example) recovered in the inert material screening step, and 200 g of the inert material before the screening (hereinafter referred to as the "extracted material 1"; Comparative Example 1). For measurement of the pressure loss, the inert material was loaded into a superficial reaction tube (q 25 mm, 3,098 mm) at a loading rate of about 40 sec/m, and after the loading of the inert material, the pressure loss was measured at an air flow rate of 30 NL/min.

Also, assuming that the extracted material 1 would have been loaded and reused in the inert material layer repeatedly, i.e., a plurality of times, a pressure loss in the inert material layer of the reactor was similarly measured using 200 g of an inert material (hereinafter referred to as the "extracted material 2"; Comparative Example 2) that was a mixture of a good material and a defective material that had been previously separated, their proportions being 70% and 30% (by weight), respectively. The pressure loss was measured three times for each inert material.

Figure 1:
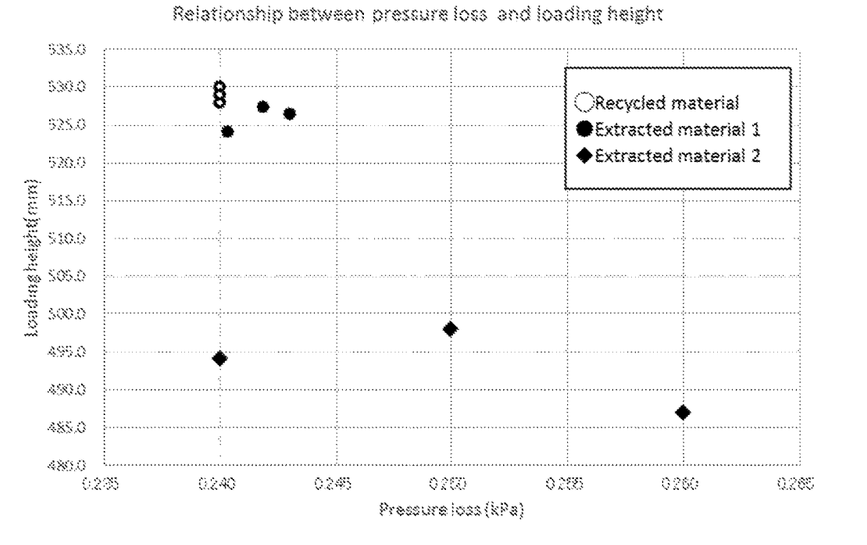
FIG. 1 is a scatter diagram showing the result of comparison between pressure losses of recycled materials and extracted materials measured in the section "Examples."

The results are shown in Table 3 and FIG. 1. Note that, in Table 3, the "pressure loss per unit layer length (kPa/m)" is a value obtained by dividing the measured pressure loss (kPa) by a loading height (m).

TABLE 3

| Sample | Inert material (g) | Loading height (mm) | Pressure loss (kPa) | Pressure loss per unit layer length (kPa/m) |
|---|---|---|---|---|
| Recycled material (Example) | 200.0 | 530.0 | 0.240 | 0.453 |
| | | 528.0 | 0.240 | 0.455 |
| | | 529.0 | 0.240 | 0.454 |
| Extracted material 1 (Comparative Example 1) | 200.0 | 526.4 | 0.243 | 0.462 |
| | | 524.1 | 0.240 | 0.459 |
| | | 527.3 | 0.242 | 0.459 |
| Extracted material 2 (Comparative Example 2) | 200.0 | 487.0 | 0.260 | 0.534 |
| | | 498.0 | 0.250 | 0.502 |
| | | 494.0 | 0.240 | 0.486 |

As can be seen from the results of the extracted material 1 which was not subjected to the screening step and the extracted material 2 for which it was assumed that the extracted material 2 would have been similarly reused repeatedly, i.e., a plurality of times, contamination with a deformed inert material causes a decrease in the loading height (layer length), resulting in an increase in pressure loss and an increase in unevenness of pressure loss. Meanwhile, the recycled inert material is obtained by removing deformed inert materials by the screening step, and therefore, as indicated by the above results, when the same amount of the inert material is loaded, the use of the recycled material can further reduce unevenness of pressure loss while an appropriate loading height is maintained.

The invention claimed is:

1. A method of recovering an inert material loaded in a fixed-bed reactor, comprising the steps of:
   extracting the inert material from the fixed-bed reactor;
   washing the extracted inert material; and
   screening the washed inert material,
   wherein, in the fixed-bed reactor, the inert material is loaded in an inert material layer provided between a first-stage catalyst layer and a second-stage catalyst layer, the first-stage catalyst layer is loaded with a first-stage catalyst for producing acrolein from propylene, and the second-stage catalyst layer is loaded with a second-stage catalyst for producing acrylic acid from acrolein,
   the inert material has a hollow cylindrical shape, and a cross-sectional circular shape of the inert material recovered through the screening step satisfies the following criteria:
   (1) the outer diameter is within ±20% of a reference value before use;
   (2) an impurity sticking to the surface and inside of the material, where the thickness of the impurity is 1.0 mm or more, is not contained; and
   (3) a clearance at a seam is 4 mm or less if the inert material has a seam.

2. The method according to claim 1, wherein the screening step comprises the steps of:
   determining quality for screening the inert material based on the criteria, and then separating the inert material.

3. The method according to claim 2, wherein a determination means is used in the determination step, and an image processing device is used as the determination means.

4. A method of producing acrylic acid, comprising the steps of:
   recovering the inert material by the method according to claim 1; and
   subjecting propylene to catalytic gas phase oxidation by introducing the propylene into a fixed-bed reactor having a first-stage catalyst layer loaded with a first-stage catalyst for producing acrolein from propylene, a second-stage catalyst layer loaded with a second-stage catalyst for producing acrylic acid from acrolein, and an inert material layer provided between the first-stage catalyst layer and the second-stage catalyst layer and loaded with at least a portion of the recovered inert material.

5. A method of producing acrylic acid, comprising the steps of:
   recovering the inert material by the method according to claim 2; and
   subjecting propylene to catalytic gas phase oxidation by introducing the propylene into a fixed-bed reactor having a first-stage catalyst layer loaded with a first-stage catalyst for producing acrolein from propylene, a second-stage catalyst layer loaded with a second-stage catalyst for producing acrylic acid from acrolein, and an inert material layer provided between the first-stage catalyst layer and the second-stage catalyst layer and loaded with at least a portion of the recovered inert material.

\* \* \* \* \*